United States Patent [19]

Ishii et al.

[11] Patent Number: 5,129,937
[45] Date of Patent: Jul. 14, 1992

[54] PYRIDYLOXYPYRIMIDINE DERIVATIVES, PREPARATION PROCESS THEREOF, AND HERBICIDAL COMPOSITIONS CONTAINING THE SAME AS ACTIVE INGREDIENTS

[75] Inventors: Tsutomu Ishii; Katsutoshi Ishikawa; Masatoshi Gohbara; Yasunaga Iwasaki; Makoto Nishida, all of Mobara, Japan

[73] Assignee: Mitsui Toatsu Chemicals Incorporated, Tokyo, Japan

[21] Appl. No.: 630,983

[22] Filed: Dec. 21, 1990

[30] Foreign Application Priority Data

Dec. 26, 1989 [JP] Japan .................................. 1-334823

[51] Int. Cl.$^5$ .................... A01N 43/54; C07D 401/12
[52] U.S. Cl. .......................... 71/92; 544/300; 546/268
[58] Field of Search ............................ 544/300; 71/92

[56] References Cited

U.S. PATENT DOCUMENTS

| | | | |
|---|---|---|---|
| 4,770,691 | 9/1988 | Nezu et al. | 544/300 |
| 4,832,729 | 5/1989 | Shigematsu et al. | 544/300 |
| 4,889,552 | 12/1989 | Wada et al. | 544/301 |
| 4,923,501 | 5/1990 | Saito et al. | 71/92 |
| 4,969,949 | 11/1990 | Shigematsu et al. | 71/92 |
| 4,985,066 | 1/1991 | Wada et al. | 544/299 |
| 5,006,155 | 4/1991 | Rheinheimer et al. | 71/92 |
| 5,015,285 | 5/1991 | Rheinheimer et al. | 71/92 |

FOREIGN PATENT DOCUMENTS

| | | |
|---|---|---|
| 0249707 | 12/1987 | European Pat. Off. . |
| 0335409 | 10/1989 | European Pat. Off. . |
| 0360163 | 3/1990 | European Pat. Off. . |
| 290671 | 11/1989 | Japan .................................. 544/300 |

Primary Examiner—Mukund J. Shah
Assistant Examiner—E. Bernhardt
Attorney, Agent, or Firm—Millen, White & Zelano

[57] ABSTRACT

Herbicidally active pyridyloxypyrimidines represented by the following formula [I]:

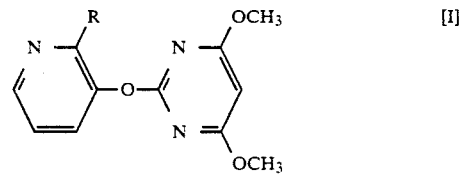

wherein R means a formyl group or an acetal group represented by

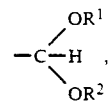

$R^1$ and $R^2$ being the same or different and individually denoting an alkyl group having 1-4 carbon atoms or $R^1$ and $R^2$ being coupled together and denoting an alkylene group, $R^3$, having 2-3 carbon atoms; are prepared by reacting 2 formyl-3-hydroxypyridine or 3-hydroxy-2-pyridine carboxaldehyde acetal with 2 halogeno-4,6 dimethoxypyrimidine in the presence of a base.

2 Claims, No Drawings

PYRIDYLOXYPYRIMIDINE DERIVATIVES, PREPARATION PROCESS THEREOF, AND HERBICIDAL COMPOSITIONS CONTAINING THE SAME AS ACTIVE INGREDIENTS

BACKGROUND OF THE INVENTION (i) Field of the Invention

The present invention relates to novel pyridyloxypyrimidine derivatives, preparation process thereof, and herbicidal compositions containing one or more of the derivatives as an active ingredient.

(ii) Description of the Related Art

Pyrimidine derivatives having a pyridyloxyl group at the 2-position are known to possess herbicidal activities as disclosed, for example, in Japanese Patent Laid-Open No. 000084/1989, Japanese Patent Laid-Open No. 210202/1989, and Japanese Patent Laid-Open No. 250378/1989.

However, the compounds described in these publications are limited to those having carboxylic acid group or groups or ester or esters thereof as the substituents on the pyridine ring and the other substituents are not investigated at all in the above publications. Further these compounds are accompanied by the practical problem that, when used as herbicides, they give injury to some crops and do not have sufficient selectivity.

SUMMARY OF THE INVENTION

The present inventors have proceeded with an extensive investigation with a view toward overcoming the above-described problem. As a result, it has been found that pyridyloxypyrimidine derivatives of a specific structure have excellent herbicidal effects and are usable with excellent safety for crops such as soybean (*Glycine max*) cotton (*Gossypium indicum*) and corn (*Zea maize*).

A first object of the invention is to provide novel pyridyloxypyrimidine derivatives.

A second object of the invention is to provide a process for the preparation of the pyridyloxypyrimidine derivatives.

A third object of the invention is to provide selective herbicidal compositions which can exhibit excellent herbicidal effects against weeds but do not give injury to economic crops.

Novel compounds of the invention are pyridyloxypyrimidine derivatives represented by the following formula [I]:

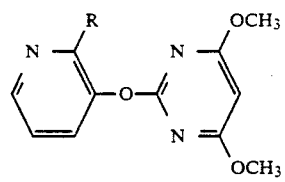

wherein R means a formyl group or an acetal group represented by

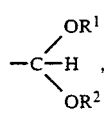

$R^1$ and $R^2$ being the same or different and individually denoting an alkyl group having 1–4 carbon atoms or $R^1$ and $R^2$ being coupled together and denoting an alkylene group, $R^3$, having 2–3 carbon atoms.

In the present invention, the above pyridyloxypyrimidine derivatives can be prepared in the following manner.

In the case of the pyridyloxypyrimidine derivative of the formula [I] in which R represents a formyl group, namely, 2-(2-formyl-3-pyridyloxy)-4,6-dimethoxypyrimidines represented by the following formula:

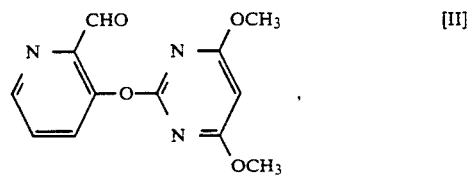

the compound can be obtained by either one of the following processes A and B:

Process A

2-Formyl-3-hydroxypyridine represented by the following formula [III]:

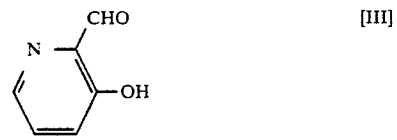

and a 2-halogeno-4,6-dimethoxypyrimidine represented by the following formula [IV]:

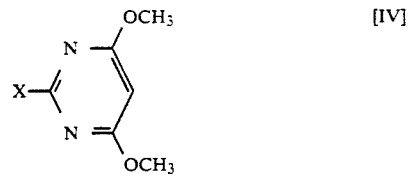

wherein X represents a chlorine, bromine or iodine atom are reacted in the presence of a base.

Process B

The formyl group of 2-formyl-3-hydroxypyridine represented by the formula [III] is converted to an acetal group represented by

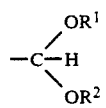

to form a 3-hydroxy-2-pyridinecarboxaldehyde acetal represented by the following formula [V]:

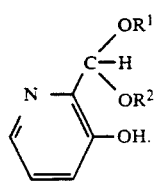

The 3-hydroxy-2-pyridinecarboxaldehyde acetal is reacted with a 2-halogeno-4,6-dimethoxypyrimidine of the formula [IV] in the presence of a base to obtain a 3-(2-pyrimidinyloxy)-2-pyridinecarboxaldehyde acetal represented by the following formula [VI]:

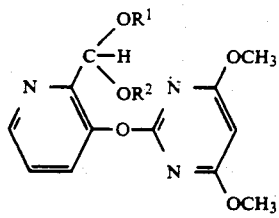
[VI]

The acetal group of the 3-(2-pyrimidinyloxy)-2-pyridinecarboxaldehyde acetal is then converted to a formyl group.

On the other hand, in the case of the pyridyloxypyrimidine derivative of the formula [I] in which R represents an acetal group, namely, 3-(2-pyrimidinyloxy)-2-pyridinecarboxaldehyde acetal represented by the formula [VI], the compound can be obtained by either one of the following processes C and D:

Process C

As described above in Process B, 3-hydroxy-2-pyridinecarboxaldehyde acetal derived from 2-formyl-3-hydroxypyridine of the formula [III] and represented by the formula [V] and a 2-halogeno-4,6-dimethoxypyrimidine of the formula [IV] are reacted in the presence of a base.

Process D

The target compound is obtained by converting the formyl group of 2-(2-formyl-3-pyridyloxy)-4,6-dimethoxypyrimidine, which is obtained above by Process A and is represented by the formula [II], to an acetal group represented by

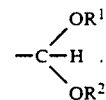

The selective herbicidal compositions according to the invention contain, as an active ingredient, one or more of the pyridyloxypyrimidine derivatives represented by the formula [I].

The herbicidal compositions of the invention exhibit marked herbicidal activities at low application rates against weed species which cause problems in agriculture, and have a broad herbicidal spectrum. Nevertheless, they can be used with extreme safety for economic crops in upland farming, such as corn, soybean and cotton. They hence exhibit outstanding selectivity. Their performance as selective herbicidal compositions is superior to the conventional herbicidal compositions. Furthermore, they can control various weeds ranging up to perennial intractable weeds by a single treatment without failure and are extremely useful herbicidal compositions.

DETAILED DESCRIPTION OF THE INVENTION AND PREFERRED EMBODIMENTS

Where R represents

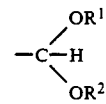

in the formula [I] and $R^1$ and $R^2$ individually denote an alkyl group, specific examples of $R^1$ and $R^2$ include methyl, ethyl, n-propyl, i-propyl, n-butyl, sec-butyl and tert-butyl groups.

Where $R^1$ and $R^2$ are coupled together to represent an alkylene group, $R^3$, specific examples of the alkylene group include ethylene, propylene and methylethylene groups.

Preparation processes of the compounds of the invention can be summarized by the following reaction scheme:

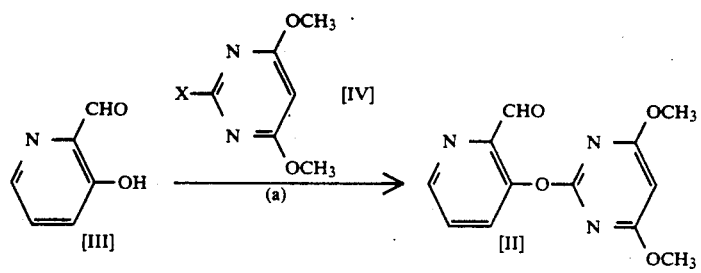

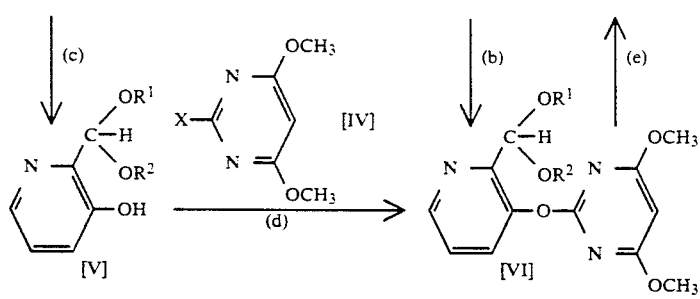
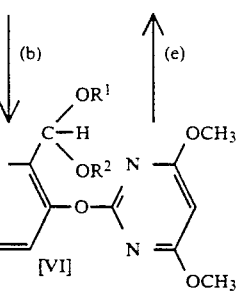

Namely, 2-(2-formyl-3-pyridyloxy)-4,6-dimethoxypyrimidine represented by the formula [II] can be prepared through the step (a) (Process A) or through the steps (c)→(d)→(e) (Process B). On the other hand, each 3-(2-pyrimidinyloxy)-2-pyridinecarboxaldehyde acetal derivative represented by the formula [VI] can be obtained through the steps (c) →(d) (Process C) or the steps (a)→(b) (Process D).

Each of the above steps will hereinafter be described in detail.

Steps (a) and (d)

The steps (a) and (d) are carried out under exactly the same conditions.

The compounds [II] and [VI] can each be prepared by heating the corresponding 3-hydroxypyridine—which is represented by the formula [VII]:

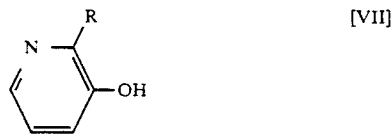

wherein R has the same meaning as defined in the formula [I], the compound [III] is indicated when R represents a formyl group and the compound [V] is meant when R denotes an acetal group—together with a 2-halogeno-4,6-dimethoxypyrimidine—which is represented by the following formula [IV]:

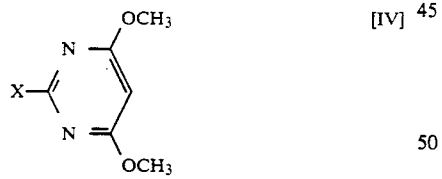

wherein X represents a chlorine, bromine or iodine atom —in an inert solvent, in the presence of a base, within the temperature range of from 50° C. to the boiling point of the solvent, for 1-10 hours.

The compound [III] can be prepared by the process disclosed in Journal of American Chemical Society, 81, 3933 (1959), while the compounds [V] can be obtained from the compound [III] through the step (c) to be described below.

Illustrative of the base include alkali metals such as metallic sodium and metallic potassium; alkali metal hydroxides such as sodium hydroxide and potassium hydroxide; and alkali metal carbonates such as sodium carbonate and potassium carbonate.

Exemplary inert solvents include aromatic hydrocarbons such as benzene, toluene and xylene; ethers such as tetrahydrofuran, dioxane and diglyme; ketones such as acetone and methyl ethyl ketone; aprotonic polar solvents such as dimethylformamide, dimethylacetamide, dimethylimidazolidinone and dimethylsulfoxide; acetonitrile; and water.

Steps (b) and (c)

The steps (b) and (c) are conducted under exactly the same conditions. In general, processes for converting a formyl group to an acetal group can all be applied. These processes will next be described specifically.

(i) Process in which an alcohol is reacted in the presence of an acid catalyst:

A corresponding alcohol is reacted in the presence of an acid. The alcohol can be used in an amount ranging from its stoichiometric amount to a large excess, the latter including a portion employed as a solvent. Illustrative of a reaction solvent include aromatic hydrocarbons such as benzene, toluene and xylene; ethers such as tetrahydrofuran, dioxane and diglyme; aprotonic polar solvents such as dimethylformamide, dimethylacetamide, dimethylimidazolidinone and dimethylsulfoxide; and acetonitrile.

Use of a dihydric alcohol such as ethylene glycol or propylene glycol as an alcohol makes it possible to convert the formyl group to a cyclic acetal group in which $R^1$ and $R^2$ of

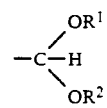

are coupled together into an alkylene group, $R^3$.

Illustrative of the acid include mineral acid such as hydrochloric acid and sulfuric acid; and organic sulfonic acids such as methanesulfonic acid, benzenesulfonic acid and p-toluenesulfonic acid. The reaction temperature may range from 0° C. to the boiling point. It is however desirable to conduct the reaction within the range of from 20° C. to the boiling point. The reaction can generally be brought to completion in 1-10 hours although the reaction time varies depending on the reaction temperature.

(ii) Process in which an orthoformate ester is reacted:

An acetal can also be obtained easily by reacting a corresponding orthoformate ester. The orthoformate ester can be used in an excess amount including a portion employed as a solvent, or the corresponding alcohol can be employed as a solvent. Other solvent inert to the reaction may also be used in some instances. In many cases, the reaction is allowed to smoothly proceed by the addition of a weakly acidic substance such as ammonium chloride as a catalyst. It is desirable to conduct the reaction at a temperature of from 50° C. to the boiling point, although the reaction temperature may range from 0° C. to the boiling point. The reaction is generally brought to completion in 2-8 hours.

(iii) Transacetalation:

To obtain an asymmetric acetal, transacetalation is conducted on a symmetric acetal obtained by the process (i) or (ii). Namely, reaction of the symmetric acetal with a higher alcohol in the presence of an acid can yield an asymmetric acetal in which one of the alkoxyl groups of the symmetric acetal has been replaced. The acid employed as a catalyst is similar to that referred to above in the process (i). The corresponding alcohol can be used in an excess amount. As an alternative, a solvent inert to the reaction can also be employed. A similar solvent to that mentioned above in the process (i) can be used as the solvent. In this reaction, a symmetric acetal in which both the alkoxyl group of the starting symmetric acetal have been replaced is also byproduced. The reaction temperature may range from 20° C. to the boiling point, whereas the reaction time may range from 2 hours to 10 hours.

Step (e)

Conventional reaction conditions for converting an acetal to its corresponding aldehyde can be used. Use of a mineral acid such as hydrochloric acid or sulfuric acid however cannot bring about an excellent yield. It is desirable to conduct the reaction under mild conditions while using a weak acid or N-hydroxybenzenesulfonamide. Particularly preferred is N-hydroxybenzenesulfonamide. The reaction is conducted by dissolving a acetal in a water-containing solvent which is inert to the reaction, adding a weak acid or N-hydroxybenzenesulfonamide, and then maintaining the reaction mixture at 0-100° C., desirably at 20-80° C. The reaction time may range from 30 minutes to 5 hours, but the reaction is usually brought to completion in 1-2 hours.

Herbicidal compositions of the invention, which contains one or more of the compounds represented by the formula [I], act extremely effectively against harmful weeds which cause problems in paddy fields or upland fields. In paddy fields, they show extremely good herbicidal effects against very troublesome gramineous weeds such as barnyardgrass, *Leersia oryzoides* and common reed; very troublesome cyperaceous weeds such as yellow nutsedge, smallflower umbrellaplant, *Cyperus serovinus*, bulrush, *Scirpus nipponicus*, *Eleocharis kuroguwai*, slender spikerush and *Fimbristylis miliacea*; very troublesome arrowhead weeds such as *Sagittaria pygmaea*, arrowhead and narrowleaf waterplantain; and broadleaf weeds such as *Monochoria vaginalis*, toothcup and parsnip. In upland fields, they exhibit superb herbicidal effects against broadleaf weeds such as common chickweed, common lambsquarters, shepherd's purse, redroot pigweed, hemp sesbania and velvetleaf; gramineous weeds such as barnyardgrass, green foxtail, large crabgrass, goosegrass, annual bluegrass, foxtail meadow, oat, wild oat, quackgrass, downy brome, bermudagrass, creeping bentgrass, broomsedge, silky bentgrass, singlegrass, fall panicum, johnsongrass, shattercane and woolly cupgrass; cyperaceous weeds such as rice flatsedge; especially perennial intractable weeds such as johnsongrass, shattercane and orchardgrass.

In an enzyme-level activity inhibitory test on ALS (acetolactate synthase), which is believed to be a target site of the compounds of the invention represented by the formula [I], the herbicidal compositions containing one or more of the compounds of the invention were found to show high inhibitory activities against weeds such as barnyardgrass, johnsongrass and green foxtail, as will be understood from the results of the test to be described later in Test 1. In contrast, they do not show inhibitory activities against broadleaf crops such as pea, cotton and peanut. These results indicate that pea, cotton, peanut and the like show high tolerance against the herbicidal compositions according to the invention. In pot tests, they were also found to show no injury or even if any, extremely slight injury against crops such as corn, soybean, cotton, beet, peanut, common sunflower, rape, potato and greens. Depending on the method of application, they can also be used, without any injury, for gramineous crops such as wheat, rice, barley and sugar cane. It is however to be noted that use of the herbicidal compositions of the invention is not limited to these crops.

The herbicidal compositions containing one or more of the compounds of the invention, which are represented by the formula [I], are effective in all application methods such as soil application, soil incorporation, foliar application and band application. They can be used at an application rate in the wide range of from 0.01 kg/ha to 10 kg/ha in terms of active ingredient. As a standard, it is however preferred to use them at an application rate of from 0.1 kg/ha to 5 kg/ha.

Incidentally, the compounds of the invention are also useful as intermediates for pyridyloxypyrimidine herbicides.

Upon application of the compounds of the formula [I] according to this invention as herbicides, they may be applied neat to weeds to be treated. In general, they are however mixed with an inert liquid carrier or solid carrier and formed into a commonly-used formulation such as powder, granules, wettable powder, emulsion or flowable formulation. One or more adjuvants can also be added if necessary for formulation.

Any carrier can be used as long as it is usable in conventional agricultural or horticultural chemicals, no matter whether it is solid or liquid. No particular limitation is therefore imposed on the carrier.

Exemplary solid carriers include mineral powders such as clay, talc, bentonite, calcium carbonate, diatomaceous earth and white carbon; organic powders such as corn tips, soybean flour and starch; high molecular compounds such as petroleum resins, polyvinyl alcohol and polyalkylene glycols; urea; and waxes. Illustrative liquid carriers include various organic solvents such as xylene, methylnaphthalene and alkylbenzenes; various oils such as vegetable oils; and water.

As adjuvants, surfactants, binders (e.g., lignine sulfonic acid, alginic acid, polyvinyl alcohol, gum arabic, sodium CMC), stabilizers (e.g., phenol compounds, thiol compounds and higher fatty acid esters for the prevention of oxidation; phosphate salts as pH regulators; and in some instances, light stabilizers), and the like—which are generally used in agricultural or horticultural chemicals—can be used either singly or in combination. In some instances, industrial fungicides, antiseptics and the like can also be incorporated for the control of bacteria and fungi.

As exemplary surfactants, non-ionic, anionic, cationic and amphoteric surfactants can be used either singly or in combination as needed. Those obtained by adding ethylene oxide (for example, "X-77", trade name; or "Neugen EA80", trade name) or propylene oxide to alkyl phenols, higher alcohols, alkylnaphthols, higher fatty acids, fatty acid esters and the like can be used as preferred non-ionic surfactants. Preferred exemplary anionic surfactants include the alkylsulfonic acid salts (e.g., "Neopelex", trade name), alkyl sulfate ester, phosphate ester and the like of alkylphenols, alkylnaphthols, higher alcohols, higher fatty acids, fatty acid esters and the like. Lignine sulfonate salts (e.g., "Sunekis", trade mark) are also preferred examples.

The content of each compound of the formula [I] in the herbicidal composition according to the invention varies depending on the formulation. In general, it can be 0.05–20 wt. % in a powder, 1–50 wt. % in a wettable powder, 0.05–15 wt. % in a granule, 1–50 wt. % in an emulsion, 1–50 wt. % in a flowable formulation and 1–50 wt. % in a dry flowable formulation. Preferably, it can be 0.5–5 wt. % in a powder, 10–40 wt. % in a wettable powder, 0.5–8 wt. % in a granule, 5–20 wt. % in an emulsion, 10–30 wt. % in a flowable formulation and 10–40 wt. % in a dry flowable formulation.

The total content of adjuvants may be 0–80 wt. %. The content of the carrier is the value which is obtained by subtracting the contents of the compound as an active ingredient and of adjuvants from 100 wt. %.

The herbicidal compositions of the invention, which contain one or more of the compounds represented by the formula [I], may be formulated together with one or more other herbicides or one or more of agricultural chemicals such as fungicides, insecticides and plant growth regulators, fertilizers and soil improving agents, to say nothing of combined use therewith. Synergistic effects may be expected in some instances.

The term "other herbicides" as used herein can mean those containing one or more of the following compounds as active ingredient, although not necessarily limited thereto:
3,6-Dichloro-2-methoxybenzoic acid (dicamba)
2,5-Dichloro-3-aminobenzoic acid (amiben)
4-Chloro-2,2-dimethylvaleranilide (monalide)
3,4-Dichloropropionanilide (propanil)
3,4-Dichloro-2-methylacrylanilide (dicryl)
3,4-Dichlorocyclopropanecarboxyanilide (crypromid)
3,4-Dichloro-2-methyl-pentanilide (karsil)
N,N-Dimethyl-2,2-diphenylacetamide (diphenamide)
N-naphthylphthalamic acid (naptalam)
N-(1,1-Dimethylbenzyl)-2-bromo-tert-butylacetamide (buromobutide)
2-Benzothiazol-2-yloxy-N-methylacetanilide (mefenasate)
1,1-Dimethyl-3-phenylurea (fenuron)
3-(4-Chlorophenyl)-1,1-dimethylurea (monuron)
3-(4-Chlorophenyl)-1-methoxy-1-methylurea (monoliuron)
1-(2-Methylcyclohexyl)-3-phenylurea (siduron)
1,1-Dimethyl-3-(3-trifluoromethylphenyl)urea (fluometuron)
3-(3,4-Dichlorophenyl)-1,1-dimethylurea (diuron)
3-(3,4-Dichlorophenyl)-1-methoxy-1-methylurea (linuron)
3-(3-Chloro-4-methylphenyl)-1,1-dimethylurea (chlortoluron)
3-[3-(N-Tert-butylcarbamoyloxy)phenyl]-1,1-dimethylurea (karbutilate)
1-(α,α-Dimethylbenzyl)-3-(4-methylphenyl)urea (dymron)
3-(4-Isopropylphenyl)-1,1-dimethylurea (isoproturon)
3-(2-Benzothiazolyl)-1,3-dimethylurea (methabenzthiazuron)
3-(2-Benzothiazolyl)-1-methylurea (benzthiazuron)
3-(Hexahydro-4,7-methanoindan-5-yl)-1,1-dimethylurea (noruron)
3-[5-(1,1-Diemthylethyl)-1,3,4-thiadiazol-2-yl]-1,3-dimehtylurea (tebuthiuron)
3-(5-Tert-butylisooxazol-3-yl)-1,1-dimethylurea (isouron)
2-Chloro-4,6-bis(ethylamino)-1,3,5-triazine (simazine)
2-Chloro-4-ethylamino-6-isopropylamino-1,3,5-triazine (atrazine)
2-Chloro-4,6-bis(isopropylamino)-1,3,5-triazine (propazine)
2-(2-Chloro-4-ethylamino-1,3,5-triazin-6-yl-amino)-2-mehtylpropionitrile (cyanazine)
2-Methoxy-4,6-bis(isopropylamino)-1,3,5-triazine (prometon)
2-Methylthio-4,6-bis(ethylamino)-1,3,5-triazine (simetryne)
2-Methylthio-4,6-bis(isopropylamino)-1,3,5-triazine (prometryne)
2-Methylthio-4-methylamino-6-isopropylamino-1,3,5-triazine (ametryne)
2-Methylthio-4-isopropylamino-6-methylamino-1,3,5-triazine (desmetryne)
4-Amino-6-tert-butyl-3-methylthio-1,2,4-triazin-5(4H)-one (metribuzin)
3-Cyclohexyl-6-dimethylamino-1-methyl-1,3,5-triazin-2,4-(1H,3H)-dione (hexazinone)
2-Chloro-N-isopropylacetanilide (propachlor)
N-Methoxymethyl-2',6'-diethyl-2-chloroacetanilide (alachlor)
2-Chloro-2',6'-diethyl-N-(butoxymethyl)acetanilide (butachlor)
2-Chloro-2'-ethyl-6'-methyl-N-(2-methoxy-1-methylethyl)acetanilide (metolachlor)
N,N-Diallyl-2-chloroacetamide (allidochlor)
2,6-Dinitro-N,N-dipropyl-4-trifluoromethylaniline (trifluralin)
3,4-Dimethyl-2,6-dinitro-N-1-ethylpropylaniline (pendimethalin)
2-Chloro-N-(4-methoxy-6-methyl-1,3,5-triazin-2-ylaminocarbonyl)benzenesulfonamide (chlorosulfuron)
Methyl 2-[3-(4-methoxy-6-methyl-1,3,5-triazin-2-yl)ureidosulfonyl]benzoate (metsulfurone-methyl)
Methyl 2-[3-(4,6-dimehtylpyrimidin-2-yl)ureidosulfonyl]benzoate (sulfometuron-methyl)
Methyl 2-[3-(4,6-dimethoxypyrimidin-2-yl)ureidosulfonyl]benzoate (bensulfuron)
Ethyl 2-[3-(4-chloro-6-methoxypyrimidin-2-yl)ureidosulfonyl]benzoate (chlorinuron)
3-[(4-Methoxy-6-methyl-1,3,5-triazin-2-yl)ureidosulfonyl]-2-thiophenecarboxylic acid (thiameturon)
Isopropylamine 2-(4-isopropyl-4-methyl-5-oxo-2-imidazolin-2-yl)nicotinate (imazapyr)
2-(4-Isopropyl-4-methyl-5-oxo-2-imidazolin-2-yl)-3-quinolic acid (imazaquin)
2-(4-Isopropyl-4-methyl-5-oxo-2-imidazolin-2-yl)-5-ethyl-3-pyridinecarboxylic acid (imazethapyr)
Methyl 2-(4-isopropyl-4-methyl-5-oxo-2-imidazolin-2-yl)-3(4)-benzoate (imazamethabenzo)
3-Isopropyl-1H-2,1,3-benzothiazin-4(3H)-one-2,2-dioxide (bentazon)
5-Bromo-3-sec-butyl-6-methyluracil (bromacil)
3,5-Dibromo-4-hydroxybenzonitrile (bromoxynil)
4-Hydroxy-3,5-iodobenzonitrile (ioxynil)
N-(Phosphonomethyl)glycine (glyphosate)

EXAMPLES

Preparation of certain compounds according to the invention will next be described specifically by the following examples.

Example 1

Synthesis of 4,6-dimethoxy-2-(2-formyl-3-pyridyloxy)pyrimidine (Compound No. 1) [Step (a)]

2-Formyl-3-hydroxypyridine (12.3 g) was dissolved in 100 ml of dimethylformamide, followed by the addition of 4.0 g of 60% sodium hydride in small portions. The resultant mixture was stirred at room temperature for a while. After bubbling subsided, 17.5 g of 2-chloro-4,6-dimethoxypyrimidine were added, followed by heating to 100° C. Subsequent to heating at the same temperature for 3 hours, dimethylformamide was recovered under reduced pressure. The residue was fractionated by chromatography on a silica gel column (solvent: n-hexane/ethyl acetate=7/3), whereby 15 g of the target compound, 4,6-dimethoxy-2-(2-formyl-3-pyridyloxy)pyrimidine, were obtained as crystals having 96–98° C. mp.

IR (KBr) (cm$^{-1}$): 2720, 1710.

NMR (CDCl$_3$) 3.80(6H,s), 5.81(1H,s), 7.59(1H,dd,J=4.3 Hz,8.1 Hz), 7.68(1H,dd,J=1.6 Hz,8.1 Hz), 8.71(1H,dd,J=1.6 Hz,4.3 Hz), 10.15(1H,s).

Example 2

Synthesis of 3-(4.6-dimethoxy-2-pyrimidinyloxy)-2-pyridinecarboxaldehyde dimethylacetal (Compound No. 2) Step (b)]

A mixture consisting of 53.0 g of 3-(4,6-dimethoxy-2-pyrimidinyloxy)-2-formylpyridine, 30.7 g of ethyl orthoformate, 0.48 g of ammonium chloride and 500 ml of methanol was heated under stirring at a reflux point for 5 hours. After the reaction mixture was cooled to room temperature, the precipitate was filtered off. The filtrate was concentrated under reduced pressure so that 56.1 g of 3-(4,6-dimethoxy-2-pyrimidinyloxy-2-pyridinecarboxaldehyde dimethylacetal were obtained (yield: 90%). A purified product was obtained by chromatography on a silica gel column.

Example 3

Synthesis of 3-(4.6-dimethoxy-2-pyrimidinyloxy)-2-pyridinecarboxaldehyde isopropylmethylacetal (Compound No. 5) transacetalation]

Added to 50 ml of toluene were 2.00 g of 3-(4,6-dimethoxy-2-pyrimidinyloxy)-2-pyridinecarboxaldehyde dimethyl acetal, 0.39 g of isopropyl alcohol and a catalytic amount (0.05 g) of p-toluenesulfonic acid. Using a reflux condenser equipped with a water trap, the resultant mixture was refluxed for 4 hours. Resulting methanol was removed through the water trap. After completion of the reaction, the solvent was distilled out under reduced pressure and the residue was purified by chromatography on a silica gel column, whereby 0.85 g of 3-(4,6-dimethoxy-2-pyrimidinyloxy)2-pyridinecarboxaldehyde isopropylmethylacetal was obtained (yield: 41%).

Example 4

Synthesis of 3-hydroxy-2-(4-methyl-1,3-dioxoran-2-yl)pyridine (intermediate) [Step (c)]

Added to 50 ml of toluene were 2.00 g (16.3 ml) of 2-formyl-3-hydroxypyridine, 1.85 g (24.4 mmol) of 1,2-propanediol and a catalytic amount (0.05 g) of p-toluenesulfonic acid. Using a reflux condenser equipped with a water trap, the resultant mixture was refluxed under stirring to remove water. The reaction was terminated 6 hours later, the reaction mixture was concentrated, and the residue was purified by chromatography on a silica gel column, whereby 1.43 g of 3-hydroxy-2-(4-methyl-1,3-dioxoran-2-yl)pyridine were obtained (yield: 48.6%).

Example 5

Synthesis of 3-(4,6-dimethoxy-2-pyrimidinyloxy)-2-pyridinecarboxaldehyde diethylacetal (Compound No. 3) Step (d)]

Sodium hydride (7.0 g) was added under stirring to 300 ml of dimethylimidazolidinone, followed by the gradual addition of 37.5 g of 3-hydroxy-2-pyridinecarboxaldehyde diethylacetal at room temperature. Heat was evolved with bubbling so that the temperature of the mixture arose to 55° C. After the mixture was heated for 1 hour at 90–95° C., 31.6 g of 2-chloro-4,6-dimethoxypyrimidine were added. The reaction mixture was heated at 100–120° C. for 8 hours so that the reaction was brought to completion. The reaction mixture was cooled to room temperature, added with 500 ml of water, and then extracted three times with 700 ml portions of ethyl acetate. The organic layers were combined, washed with water and then dried over anhydrous sodium sulfate. The solvent was then distilled out, whereby 87.4 g of an oily residue were obtained. The residue was purified by silica gel chromatography (n-hexane/ethyl acetate=1:1) so that 54.6 g of 3-(4,6-dimethoxy-2-pyrimidinyloxy)-2-pyridinecarboxaldehyde diethylacetate were obtained (yield: 90%).

Example 6

Synthesis of 4,6-dimethoxy-2-(2-formyl-3-pyridyloxy)pyrimidine (Compound No. 1) [Step (e)]

To a mixture consisting of 400 ml of dioxane and 400 ml of water, 42.6 g of 3-(4,6-dimethoxy-2-pyrimidinyloxy)-2-pyridinecarboxaldehyde diethylacetal and 22 g of N-hydroxybenzenesulfonamide were added under stirring. The reaction mixture was heated at 80–85° C. for 1 hour so that the reaction was brought to completion. Low-boiling substances were then distilled completion. Low-boiling substances were then distilled out under reduced pressure. The residue was added and extracted with 300 ml of saline and 300 ml of ethyl acetate. The organic layer was dried over sodium sulfate and then concentrated under reduced pressure, whereby 56.6 g of an oily residue was obtained. The residue was purified by chromatography on a silica gel column (n-hexane/ethyl acetate=1:1) so that 19.2 g of 4,6-dimethoxy-2-(2-formyl-3-pyridyloxy)pyrimidine were obtained (yield: 54%).

The compounds of the invention prepared in accordance with their procedures in the examples are summarized in Table 1. It is to be noted that Compound Nos.

4, 6, 7 and 8 were prepared through the following synthesis routes, respectively:

| Compound No. 4: | Step (a) → Step (b). |
|---|---|
| Compound No. 6: | An intermediate was prepared in a similar manner to Example 4, and Step (d) was then conducted. |
| Compound No. 7: | Step (d) was conducted using the intermediate obtained in Example 4. |
| Compound No. 8: | An intermediate was prepared in a similar manner to Example 4, and Step (d) was then conducted. |

Formulation Example 2: (Wettable powder)

A wettable powder was obtained by thoroughly grinding and mixing 20 parts by weight of Compound No. 7 of the invention, 2 parts by weight of sodium alkylbenzenesulfonate, 1 part by weight of polyoxyethylene alkylphenyl ether and 77 parts by weight of "Zeaklite" (trade name of silica supplied from Zeaklite Kogyo Industries, Ltd.).

Formulation Example 3: (Wettable powder)

A wettable powder was obtained by thoroughly grinding and mixing 50 parts by weight of Compound No. 6 of the invention, 5 parts by weight of white carbon, 6 parts by weight of polyoxyethylene alkylphenyl ether, 2 parts by weight of sodium lignine sulfonate and 37 parts by weight of diatomaceous earth in a Jet-O-Miser.

Formulation Example 4: (Flowable formulation)

A flowable formulation was obtained by adding 76.7 parts by weight of water to the mixture of 20 parts by weight of Compound No. 1 of the invention, 2 parts by weight of sodium lignine sulfonate, 0.3 part by weight of xanthan gum and 1 part by weight of polyoxyethylene alkylaryl ether, mixing them and then finely grinding the resultant mixture in a sand grinder.

Formulation Example 5: (Flowable formulation)

A flowable formulation was obtained by wet grinding and mixing 30 parts by weight of Compound No. 2 of

TABLE 1

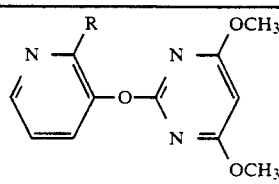

(I)

| Compound No. | Substituents R¹ | R² | Melting point (°C.) | NMR(CHCl₃; δ from TMS) (400 MHz) |
|---|---|---|---|---|
| 2 | Me | Me | Oily matter | 3.36(6H, s); 3.81(6H, s); 5.73(1H, s); 5.79(1H, s); 7.35–7.39(1H, m); 7.55–7.57(1H, m); 8.55–8.57(1H, d, j=4.4Hz) |
| 3 | Et | Et | 76.8–77.6 | 1.05(6H, t, j=7.3Hz); 3.54(4H, q, j=7.3Hz); 3.72(6H, s); 5.70(1H, s); 5.74(1H, s); 7.24–7.27(1H, m); 7.43–7.45(1H, m); 8.49–8.51(1H, m) |
| 4 | n-Bu | n-Bu | Oily matter | 0.86(6H, t, J=7.3Hz); 1.24–1.35(4H, m); 1.40–1.52(4H, m); 3.40–3.50(4H, m); 3.79(6H, s); 5.71(1H, s); 5.75(1H, s); 7.35–7.41(1H, m); 7.55–7.58(1H, m); 8.50–8.52(1H, m) |
| 5 | Me | i-Pr | Oily matter | 1.12(3H, d, j=5.9Hz); 1.20(3H, d, j=5.9Hz); 3.30(3H, s); 3.80(6H, s); 3.91–4.00(1H, m); 5.73(1H, s); 5.76(1H, s); 7.30–7.35(1H, m); 7.59–7.61(1H, m); 8.53–8.55(1H, m); |
| 6 | —CH₂—CH₂— | | 76–78 | 3.79(6H, s); 3.97–4.01(2H, m); 4.21–4.25(2H, m); 5.78(1H, s); 6.11(1H, s); 7.34(1H, dd, j=3.7 and 8.1Hz); 7.55(1H, d, j=8.1Hz); 8.51(1H, d, j=3.7Hz) |
| 7 | CH₃<br>\|<br>—CH—CH₂— | | Oily matter | 1.25(1.5H, d, j=5.9Hz); 1.34(1.5H, d, j=6.6H); 3.44–3.48(0.5H, m); 3.54–3.57(0.5H, m); 4.02–4.05(0.5H, m); 4.16–4.21(0.5H, m); 4.23–4.28(0.5H, m); 4.31–4.39(0.5H, m); 5.75(1H, s); 6.02(0.5H, s); 6.16(0.5H, s); 7.14–7.16(1H, d, j=8.1Hz); 7.21–7.27(1H, m); 7.33–7.39(1H, m) |
| 8 | —CH₂—CH₂—CH₂— | | Oily Matter | 1.40(1H, d, j=13.9Hz); 2.6–2.87(1H, m); 3.81(6H, s); 3.91–3.97(2H, m); 4.20–4.24(2H, m); 5.79(1H, s); 5.85(1H, s); 7.35(1H, dd, j=4.4 and 8.1Hz); 7.58(1H, d, j=8.1Hz); 8.57(1H, d, j=4.4Hz) |

Formulation Examples

Formulation examples of certain herbicidal compositions according to the invention will next be described.

Formulation Example 1: (Wettable powder)

A wettable powder was obtained by thoroughly grinding and mixing 20 parts by weight of Compound No. 2 of the invention, 2 parts by weight of "Neopelex" (trade mark, product of Kao Corporation; sodium dodecyl benzene sulfonate), 1 part by weight of "Neugen EA80" (trade name, product of Daiichi Kogyo Seiyaku Industries, Ltd.; polyoxyethylene nonylphenyl ether), 5 parts by weight of white carbon and 72 parts by weight of diatomaceous earth.

the invention and a solution of 10 parts by weight of "Sun Ekisu P252" (trade name, product of Sanyo-Kokusaku Pulp Co., Ltd.; sodium lignine sulfonate) in 50 parts by weight of water and then adding and mixing a solution of 0.2 part by weight of "Kelzan S" (trade name, product of Kelco Corp.; xanthan gum) in 9.6 parts by weight of water and 0.2 part by weight of "Deltop" (trade mark, product of Takeda Chemical Industries, Ltd.; organic iodine antiseptic).

Formulation Example 6: (Powder)

A powder was obtained by thoroughly grinding and mixing 1 part by weight of Compound No. 1 of the invention, 0.5 part by weight of "Emulgen 910" (trade name, product of Kao Corporation; polyoxyethylene nonylphenyl ether) and 98.5 parts by weight of kaolin clay.

Formulation Example 7: (Powder)

A powder was obtained by grinding and mixing 3 parts by weight of Compound No. 7 of the invention, 3 parts by weight of sodium lignine sulfonate, 2 parts by weight of polyoxyethylene alkylaryl ether and 92 parts by weight of clay.

Formulation Example 8: (Dry flowable formulation)

A dry flowable formulation was obtained by mixing 60 parts by weight of Compound No. 1 of the invention, which had been finely ground, 5 parts by weight of sodium alkyl benzene sulfonate, and 35 parts by weight of polypropylene glycol polyethylene glycol ether.

Formulation Example 9: (Granule)

One part by weight of Compound No. 6 of the invention, which had been finely ground, 2 parts by weight of "Neopelex" (trade mark; described above), 2 parts by weight of "Sun Ekisu P252" (trade name; described above), 70 parts by weight of bentonite and 23 parts by weight of talc were thoroughly mixed. A suitable amount of water was added to the resultant mixture to wet the same, followed by extrusion of the mass through a small injection molding machine into pellets. After the pellets were dried at 30–60° C. in air and then crushed into granules, the granules were classified by a sifting machine to collect granules of 0.3–2 mm.

Formulation Example 10: (Granule)

One part by weight of Compound No. 1 of the invention, which had been finely ground, 2 parts by weight of "Gosenol GL-O5s" (trade name, product of The Nippon Synthetic Chemical Industry Co., Ltd.; PVA), 2 parts by weight of "Sun Ekisu P-252" (trade name; described above) and 95 parts by weight of clay were thoroughly mixed. A suitable amount of water was added to the resultant mixture to wet the same, followed by extrusion of the mass through a small injection molding machine into pellets. After the pellets were dried at 60–90° C. in air and then crushed into granules, the granules were classified by a sifting machine to collect granules of 0.3–1 mm.

Formulation Example 11: (Emulsion)

Ten parts by weight of Compound No. 4 of the invention, 10 parts by weight of "Sorpole 800A" (trade name, product of Toho Chemical Industries Co., Ltd.; a nonionic/anionic surfactant mixture) and 80 parts by weight of o-xylene were mixed into an emulsion. [Herbicidal Activity Tests].

Herbicidal activity tests of certain compounds of the invention will next be described.

Test 1

ALS (Acetolactate Synthase) Inhibition Test

To determine the selectivity in enzyme level between crops and weeds, an ALS inhibition test was conducted using pea as a representative of broadleaf crops and barnyardgrass as a representative of gramineous weeds.

After seeds of pea and barnyardgrass were allowed to germinate at 25° C. for 8–14 days in a dark place, partially-purified suspensions (Suspensions A) of acetolactate syntase were separately obtained from seedlings in accordance with the method described in the literature, Plant Physiology, 75, 827–831. In a test tube, 0.5 mg of one of test compounds was weighed, followed by the addition of 0.15 ml of a 20 mM $K_2HPO_4$ solution and 0.25 ml of a reaction substrate medium which consisted of 40 mM of $K_2HPO_4$, 40 mM of sodium pyruvate, 1 mM of TPP, 1 mM of $MgCl_2$ and 20 $\mu$M of FAD so that 0.4 ml of a reaction solution (Solution B) was prepared. Added to 0.4 ml of Solution B was 0.1 ml of Suspension A. After the resultant mixture was shaken for 1 hour in a thermostat water bath controlled at 30° C., 50 $\mu$l of 6N sulfuric acid were added to terminate the reaction.

Next, the reaction-terminated liquid mixture was transferred into a thermostat water bath controlled at 60° C. and was heated for 15 minutes. Thereafter, 0.5 ml of a 0.5% creatine solution and 0.5 ml of a 5% alkaline α-naphthol solution were added, and the resultant mixture was maintained at 60° C. for 15 minutes. As a result, the test solution developed a pink-red color. After the above operation, the absorbance of the test solution at 525 nm was measured by a spectrophotometer (Absorbance ① of Test Compound).

On the other hand, the absorbance (Absorbance ②) of Blank) of a solution obtained by subjecting a portion of Solution B, said portion being free of the test compound, to the above operation and the absorbance (Absorbance ③) of sulfuric acid terminated) of another solution obtained by subjecting another portion of Solution B, said portion containing 50 $\mu$l of 6N sulfuric acid as a test compound, were measured at the same time. Based on the values of the respective measurements, the enzymoreaction inhibition rate at 10 ppm (5 $\mu$g/0.5 ml) of each compound was determined in accordance with the below-described formula. The results are shown in Table 2.

$$\text{Enzymoreaction inhibition rate} = \left(1 - \frac{①-③}{②-③}\right) \times 100$$

Incidentally, Comparative Compounds A and B means the following compounds (this also applies to Test 2 and Test 3).

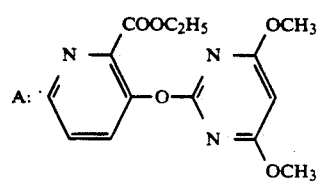

(Compound disclosed in Japanese Patent Laid-Open No. 000084/1989)

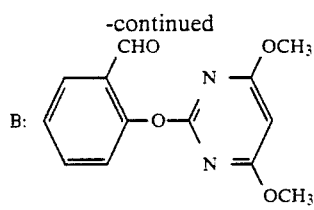

B: (Compound disclosed in Japanese Patent Laid-Open No. 174059/1987)

The results of this test indicate that the compounds of the invention show strong inhibition in enzyme level against gramineous weeds such as barnyardgrass but show no inhibition to broadleaf crops such as pea, in other words, have distinct selectivity.

TABLE 2

Results of Enzymoreaction Inhibition Test

| Compound No. | Inhibition rate (%) | |
|---|---|---|
| | Barnyardgrass | Pea |
| 1 | 100 | 3 |
| 2 | 81 | 0 |
| 3 | 84 | 0 |
| 4 | 94 | 0 |
| 5 | 100 | 0 |
| 6 | 96 | 0 |
| 7 | 87 | 0 |
| 8 | 86 | 0 |
| Comparative Compound | | |
| A | 5 | 52 |
| B | 98 | 72 |

Test 2

Upland Soil Application Test

Resin-made 1/2500-are pots were filled with the soil of an upland field. After they were fertilized, soybean, corn and cotton were seeded and 2-3 cm soil covering was applied. Seeds of redroot pigweed, morningglory (*Ipomoea purpurea*), common lambsquarters, barnyardgrass, green foxtail, large crabgrass, foxtail meadow and johnsongrass had been uniformly mixed with the soil. They were allowed to germinate in a green house. One day later (before emergence of weeds), a wettable powder prepared from a predetermined amount of each test compound in a similar manner to the method described in Formulation Example 1 was diluted with water and then sprayed evenly at an application rate equal to 10 l per are onto the surface of the soil by means of a pressure-operated ULV (ultra low volume) sprayer. Influence to the crops and weeds were observed 30 days later. The results are shown in Table 3, in which the degree of damages of each test plant and the degree of injury to each crop were determined by comparing the air-dried weights of the test plant and crop with those of the corresponding plant and crop in untreated pots and are shown in accordance with the following standard:

| Rank | Growth rate (%) expressed in terms of the percentage of dried weight relative to the dried weight of untreated group | |
|---|---|---|
| 5 | 0-5 | (Death) |
| 4 | 6-10 | (Severe damages) |
| 3 | 11-40 | (Medium damages) |
| 2 | 41-70 | (Small damages) |
| 1 | 71-90 | (Slight damages) |
| 0 | 91-100 | (No damages) |

The results of the present test indicate that the compounds of the invention represented by the formula [I] exhibit high herbicidal effects against gramineous weed including some broadleaf weeds and perennial weed in soil treatment and can be used extremely safely for crops such as soybean, cotton and corn.

Test 3

Upland Foliar Application Test

Resin-made 1/10000-are pots were filled with the soil of an upland field. Redroot pigweed, morningglory (*Ipomoea pupurea*), common lambsquarters, foxtail meadow, johnsongrass, barnyardgrass, green foxtail, large crabgrass, soybean, corn and cotton were separately seeded and were allowed to germinate in a green house. When each plant grew to the stage of 2-3 leaves, an emulsion formulated from a predetermined amount of each test compound in a similar manner to the method described in Formulation Example 11 was diluted with water and then sprayed at a predetermined application rate by means of a pressure-operated ULV (ultra low volume) sprayer. The application rate was controlled at 5 l per are. Influence to the crops and weeds were observed on the 30th day after the spray of the herbicides. The results are shown in Table 4 in which the degree of damages of each test plant and the degree of injury to each crop are shown in a similar manner to Test 2.

The results of the present test indicate that the compounds of the invention represented by the formula [I] exhibit high herbicidal effects against gramineous weeds including some broadleaf weeds and perennial weeds in foliage application and can be used extremely safely for crops such as soybean, cotton and corn.

TABLE 3

Results of Upland Soil Treatment Test

| Comp'd. No. | Application rate of active ingredient (g ai/a) | Herbicidal effects | | | | | | | Crop injury | | |
|---|---|---|---|---|---|---|---|---|---|---|---|
| | | Redroot Pigweed | Common lambquarters | Barnyardgrass (*Echinochloa crus-galli*) | Foxtail (*Setaria viridis*) | Crabgrass (*Digitaria adsendens*) | Foxtail meadow | Johnsongrass | Soybean (*Glycine max*) | Cotton (*Gossypium indicum*) | Corn (*Zea maize*) |
| 1 | 30 | 3 | 2 | 3 | 3 | 2 | 3 | 4 | 0 | 0 | 0 |
| 2 | 30 | 4 | 5 | 4 | 5 | 5 | 5 | 5 | 0 | 0 | 0 |
| 3 | 30 | 5 | 5 | 4 | 4 | 4 | 5 | 5 | 0 | 0 | 0 |
| 4 | 30 | 5 | 5 | 5 | 5 | 5 | 5 | 5 | 0 | 0 | 0 |
| 5 | 30 | 5 | 5 | 4 | 5 | 4 | 5 | 5 | 0 | 0 | 0 |
| 6 | 30 | 4 | 4 | 3 | 4 | 3 | 4 | 5 | 0 | 0 | 0 |
| 7 | 30 | 4 | 4 | 5 | 5 | 4 | 4 | 5 | 0 | 0 | 0 |
| 8 | 30 | 3 | 3 | 4 | 3 | 3 | 4 | 4 | 0 | 0 | 0 |
| Comp. Comp'd. A | 30 | 4 | 4 | 3 | 5 | 4 | 5 | 5 | 5 | 5 | 5 |

TABLE 3-continued

Results of Upland Soil Treatment Test

| Comp'd. No. | Application rate of active ingredient (g ai/a) | Redroot Pigweed | Common lamb-quarters | Barnyard-grass (Echinochloa crus-galli) | Foxtail (Setaria viridis) | Crabgrass (Digitaria adsendens) | Foxtail mead-ow | Johnson-grass | Soybean (Glycine max) | Cotton (Gossypium indicum) | Corn (Zea maize) |
|---|---|---|---|---|---|---|---|---|---|---|---|
| Comp. Comp'd. B | 30 | 3 | 3 | 3 | 4 | 4 | 4 | 4 | 5 | 5 | 5 |

TABLE 4

Results of Upland Foliar Application Test

| Comp'd. No. | Application rate of active ingredient (g ai/a) | Redroot Pigweed | Common lamb-quarters | Barnyard-grass (Echinochloa crus-galli) | Foxtail (Setaria viridis) | Crabgrass (Digitaria adsendens) | Foxtail mead-ow | Johnson-grass | Soybean (Glycine max) | Cotton (Gossypium indicum) | Corn (Zea maize) |
|---|---|---|---|---|---|---|---|---|---|---|---|
| 1 | 30 | 5 | 5 | 5 | 5 | 4 | 5 | 5 | 1 | 0 | 0 |
| 2 | 30 | 5 | 4 | 4 | 4 | 4 | 4 | 5 | 0 | 0 | 0 |
| 3 | 30 | 5 | 5 | 5 | 5 | 5 | 5 | 5 | 0 | 0 | 0 |
| 4 | 30 | 5 | 5 | 5 | 5 | 5 | 5 | 5 | 0 | 0 | 0 |
| 5 | 30 | 5 | 4 | 5 | 5 | 4 | 5 | 5 | 0 | 0 | 0 |
| 6 | 30 | 5 | 4 | 4 | 4 | 4 | 5 | 5 | 0 | 0 | 0 |
| 7 | 30 | 5 | 4 | 5 | 5 | 4 | 5 | 5 | 0 | 0 | 0 |
| 8 | 30 | 4 | 4 | 4 | 4 | 3 | 4 | 5 | 0 | 0 | 0 |
| Comp. Comp'd. A | 30 | 4 | 4 | 5 | 5 | 4 | 5 | 5 | 5 | 5 | 5 |
| Comp. Comp'd. B | 30 | 3 | 3 | 4 | 4 | 4 | 4 | 4 | 5 | 5 | 5 |

Test 4

Treatment of Soil under Submerged Condition (Preemergence Treatment)

1/5000-are Wagner pots were filled with soil. Seeds or tubers of barnyardgrass, bulrush and *Sagittaria pygmaea* were seeded or planted under submerged condition. Two pairs of rice seedlings (2-3 leaf stage), which had been reared in advance, were transplanted to each pot and were allowed to germinate in a green house. Each pair consisted of two rice seedlings. On day later (before emergence of weeds), each pot was treated with a granule which had been prepared by processing a predetermined amount of the test composition in accordance with a similar method to the method described in Formulation Example 9. The state of emergence of weeds and the state of injury of rice were observed 30 days later. The results are summarized in Table 5. In the table, the degrees of damages of the test plants and the degrees of injury of rice are shown in a similar manner to Example 2.

Test 5

Treatment of Soil under Submerged Condition (Growth-Period Treatment)

1/5000-are Wagner pots were filled with soil. Seeds or tubers of barnyardgrass, bulrush and *Sagittaria pygmaea* were seeded or planted under submerged condition. Two pairs of rice seedlings (2-3 leaf stage), which had been reared in advance, were transplanted to each pot and were allowed to grow in a green house. Each pair consisted of two rice seedlings. When the barnyardgrass grew to the two-leaf stage, each pot was treated with a granule which had been prepared by processing a predetermined amount of the test composition in accordance with a similar method to the method described in Formulation Example 9. The state of emergence of weeds and the state of injury of rice were observed 30 days later. The results are summarized in Table 6. In the table, the degrees of damages of the test plants and the degrees of injury of the rice are shown in a similar manner to Example 2.

The results of Test 4 to Test 5 indicate that the compounds of the invention represented by the formula [I] exhibit high herbicidal effects against gramineous weeds including some broadleaf weeds and perennial weeds in soil treatment under submerged condition and can be used for rice under extremely low injury conditions.

TABLE 5

Results of Submerged Soil Treatment Test (Pre-Emergence Treatment)

| Compound No. | Application rate of active ingredient (g ai/a) | Barnyardgrass (Echinochloa crus-galli) | Bulrush (Scirpus juncoides) | Arrowhead sp. (Sagittaria pygmaea) | Rice (Oryza sativa) |
|---|---|---|---|---|---|
| 1 | 30 | 4 | 4 | 4 | 1 |
| 2 | 30 | 5 | 5 | 5 | 0 |

TABLE 5-continued

Results of Submerged Soil Treatment Test (Pre-Emergence Treatment)

| Compound No. | Application rate of active ingredient (g ai/a) | Herbicidal effects | | | Crop injury |
|---|---|---|---|---|---|
| | | Barnyardgrass (*Echinochloa crus-galli*) | Bulrush (*Scirpus juncoides*) | Arrowhead sp. (*Sagittaria pygmaea*) | Rice (*Oryza sativa*) |
| 3 | 30 | 5 | 5 | 5 | 0 |
| 4 | 30 | 5 | 5 | 5 | 0 |
| 5 | 30 | 5 | 5 | 5 | 0 |
| 6 | 30 | 5 | 5 | 5 | 0 |
| 7 | 30 | 5 | 5 | 4 | 0 |
| 8 | 30 | 5 | 4 | 4 | 0 |
| Comp. Comp'd. A | 30 | 5 | 5 | 4 | 5 |
| Comp. Comp'd. B | 30 | 3 | 3 | 5 | 5 |

TABLE 6

Results of Submerged Soil Treatment Test (Growth Stage Treatment)

| Compound No. | Application rate of active ingredient (g ai/a) | Herbicidal effects | | | Crop injury |
|---|---|---|---|---|---|
| | | Barnyardgrass (*Echinochloa crus-galli*) | Bulrush (*Scirpus juncoides*) | Arrowhead sp. (*Sagittaria pygmaea*) | Rice (*Oryza sativa*) |
| 1 | 30 | 5 | 5 | 4 | 1 |
| 2 | 30 | 4 | 4 | 4 | 0 |
| 3 | 30 | 5 | 5 | 5 | 0 |
| 4 | 30 | 5 | 4 | 4 | 0 |
| 5 | 30 | 5 | 5 | 5 | 0 |
| 6 | 30 | 5 | 5 | 3 | 0 |
| 7 | 30 | 5 | 4 | 4 | 0 |
| 8 | 30 | 4 | 2 | 2 | 0 |
| Comp. Comp'd. A | 30 | 5 | 4 | 4 | 5 |
| Comp. Comp'd. B | 30 | 5 | 5 | 4 | 5 |

We claim:

1. A pyridyloxypyrimidine compound represented by the following formula:

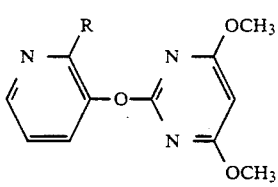

wherein R means a formyl group or an acetal group represented by

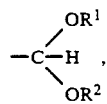

$R^1$ and $R^2$ being the same or different and individually denoting an alkyl group having 1-4 carbon atoms or $R^1$ and $R^2$ being coupled together and denoting an alkylene group, $R^3$, having 2-3 carbon atoms.

2. A herbicidal composition comprising, as an active ingredient, a pyridyloxypyrimidine compound represented by the following formula:

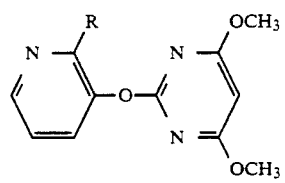

wherein R means a formyl group or an acetal group represented by

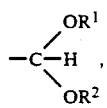

$R^1$ and $R^2$ being the same or different and individually denoting an alkyl group having 1-4 carbon atoms or $R^1$ and $R^2$ being coupled together and denoting an alkylene group, $R^3$, having 2-3 carbon atoms.

* * * * *